(12) United States Patent
Bombardelli et al.

(10) Patent No.: US 6,620,842 B2
(45) Date of Patent: Sep. 16, 2003

(54) CHALCONES

(75) Inventors: Ezio Bombardelli, Milan (IT); Piero Valenti, Bologna (IT)

(73) Assignee: Indena SpA, Milan (IT)

(*) Notice: Subject to any disclaimer, the term of this patent is extended or adjusted under 35 U.S.C. 154(b) by 0 days.

(21) Appl. No.: 10/075,626

(22) Filed: Feb. 15, 2002

(65) Prior Publication Data
US 2003/0055056 A1 Mar. 20, 2003

Related U.S. Application Data

(63) Continuation of application No. PCT/EP00/08366, filed on Aug. 28, 2000.

(30) Foreign Application Priority Data

Sep. 3, 1999 (GB) ................................. 9920910

(51) Int. Cl.⁷ ............................................... A61K 31/35
(52) U.S. Cl. ..................... 514/455; 514/456; 549/388; 549/401
(58) Field of Search ................ 549/388, 401; 514/455, 456

(56) References Cited

U.S. PATENT DOCUMENTS

| 5,525,625 A | 6/1996 | Bridges et al. ............. 514/456 |
| 5,808,137 A | 9/1998 | Bombardelli et al. ....... 560/255 |

FOREIGN PATENT DOCUMENTS

WO    WO 91/17749    11/1991

OTHER PUBLICATIONS

Verma, A.K. et al,. "Inhibition of 7,12–Dimethylbenz(α)anthracene– and N–Nitrosomethylurea–induced Rat Mammary Cancer by Dietary Flavonol Quercetin," Cancer Research 48, pp. 5754–5758, 1988.

Baird, W. et al., "Natural Products as a Source of Potential Cancer Chemotherapeutic and Chemopreventive Agents," Journal of Natural Products, 53:1, pp. 23–41, 1990.

Larocca, L.M. et al., "Type II Oestrogen Binding Sites in Acute Lymphoid and Myeloid Leukaemias: Growth Inhibitory Effect of Oestrogen and Flavonoids," British Journal of Hermatology, 75, pp. 489–495, 1990.

Scambia, G. et al., "Inhibitory Effect of Quercetin on OVCA 433 Cells and Presence of Type II Oestrogen Binding Sites in Primary Ovarian Tumours and Cultured Cells," Br. J. Cancer, 62, pp. 942–946, 1990.

Gogusev, J. et al., "Genotype Markers and Proto–Oncogene Analysis in the CD30–Positive "Malignant Histiocytosis," Del Cell Line With t(5;6)(q35;p21)," Int. J. Cancer, 46, pp. 106–112, 1990.

Scambia, G. et al., "Inhibitory Effect of Quercetin on Primary OVarian and Endometrial Cancers and Synergistic Activity with cis–Diamminedichloroplatinum(II)," Gynecologic Oncology, 45, pp. 13–19, 1992.

Skehan, P. et al., "New Colorimetric Cytotoxicity Assay for Anticancer–Drug Screening," J. Nat. Can. Inst., 82:13, pp. 1107–112, 1990.

Chem Abstracts vol., 116, No. 12.
Chem Abstracts vol. 112, No. 19.
Chem Abstracts, vol. 112, No. 5.

*Primary Examiner*—Amelia Owens
(74) *Attorney, Agent, or Firm*—Pennie & Edmonds LLP

(57) ABSTRACT

Disclosed are novel chalcone derivatives having the formula (I)

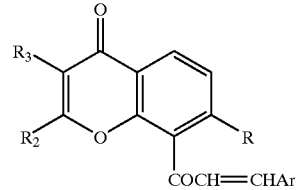

The compounds possess antiproliferative activity and are useful for the manufacture of a medicament for the treatment or prevention of neoplasms, particularly those located in the uterus, ovary or breast. The compounds of the invention may also be useful in the manufacture of a medicament for the treatment or prevention of menopausal disorders and osteoporosis.

33 Claims, No Drawings

CHALCONES

This application is a continuation of PCT/EP00/08366, filed Aug. 28, 2000.

FIELD OF THE INVENTION

The present invention relates to a novel class of compounds which have structures related to certain naturally occurring and synthetic chalcones, as well as to methods for the preparation of such compounds and to pharmaceutical uses thereof.

TECHNICAL FIELD

The compound 1,3-diphenyl-2-propene-1-one is known by the trivial name "chalcone". Many naturally occurring flavanoids share structural features with chalcone and are referred to by the generic term "chalcones". Also, certain flavanoids, including ones which are also classified as chalcones, have recently been demonstrated to have anticancer activity (Cancer Research 48, 5754, 1988) and chemopreventive activity in some tumours (J. Nat. Prod. 53, 23, 1990).

In particular, quercetin, an ubiquitous flavonoid found in plants, has been shown to act on the proliferation of human leukaemic cells (Br. J. Haematology, 75, 489, 1990) and on other cell lines (Br. J. Cancer, 62, 94, 942, 1990; Int. J. Cancer, 46, 112. 1990; Gynaecologic Oncology, 45, 13, 1992) and to possess a synergic action with common antiblastic drugs.

In addition, some natural or synthetic chalcones, described in our International Patent Publication No. WO 91/17749, and in International Patent Publication No. WO 96/19209 (Baylor College of Medicine), have proved to have a significant antiproliferation activity on a variety of different cell lines.

SUMMARY OF THE INVENTION

Thus according to one aspect of the present invention, there is provided a compound of Formula (I):

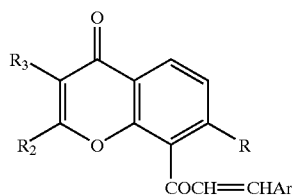

The action in vivo of these polyphenol substances is certainly much more complicated. All these compounds are generally characterised by an almost complete insolubility in water and, in vivo, by a very poor bioavailability linked to a rapid metabolism of phenols and a marked affinity for lipids and proteins.

Surprisingly, it has now been found that certain novel chalcones, chalcone derivatives and chalcone analogues, and in particular, compounds in which the phenyl ring in the 1-position is substituted or replaced by rings containing one or more heteroatoms, possess a greater antiproliferation activity both on sensitive cancerous cells and on cells which are resistant to common chemotherapeutic drugs, including the latest generation anti-neoplastic agents, paclitaxel and docetaxel.

Thus according to one aspect of the present invention, there is provided a compound of Formula (I):

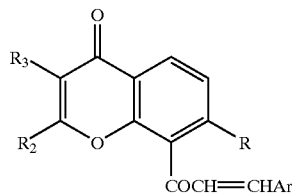

or a pharmaceutically acceptable salt or solvate thereof wherein:

Ar represents
  a substituted or unsubstituted, (preferably aromatic), carbocyclic or heterocyclic group, said carbocyclic or heterocyclic group containing from 5 to 10 ring atoms, said ring atoms forming one or two rings, wherein the or each ring contains 5 or 6 ring atoms, any heteroatoms being selected from N, O and S, any substituents on the Ar group being independently selected from the group consisting of.
    (a) Cl, (b) Br, (c) F, (d) OH, (e) $NO_2$, (f) $CF_3$, (g) $C_{1-4}$lower alkyl (in particular $CH_3$), (h) $SCH_3$, (i) $NHCOCH_3$, (j) $N(R^6)(R^8)$ wherein $R^6$ and $R^8$ are the same or different and each represents H or lower $C_{1-4}$alkyl, (k) $OR^{10}$ wherein $R^{10}$ represents a saturated or unsaturated lower $C_{1-6}$ straight or branched hydrocarbyl group which may be unsubstituted or substituted by 1, 2 or 3 substituents selected from: Cl, Br, F, OMe, $NO_2$ and $CF_3$, and (l) —$OCOR^{11}$, wherein $R^{11}$ represents a saturated or unsaturated lower $C_{1-6}$ straight or branched hydrocarbyl group or a phenyl group;

R represents
  OH, $OR^{10}$ or $OCOR^{11}$, wherein $R^{10}$ and $R^{11}$ are as defined above; and (A) $R^2$ and $R^3$ are each independently selected from:
  (i) a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of:
    Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^{6,}$ $R^8$, $R^{10}$ and $R^{11}$ are as defined above,
  (ii) Cl, (iii) Br, (iv) F, (v) OH, (vi) $NO_2$, (vii) a saturated or unsaturated lower Cl straight or branched hydrocarbyl group which may be unsubstituted or substituted by 1, 2 or 3 substituents selected from Cl, Br, F, OMe, $NO_2$ and $CF_3$, (viii) $NHCOCH_3$, (ix) $N(R^6)(R^8)$, (x) $SR^{10}$, (xi) $OR^{10}$, and (xii) $OCOR^{11}$, wherein $R^6$, $R^8$, $R^{10}$ and $R^{11}$ are as defined above; or (B) $R_2$ and $R_3$ taken together with the carbon atoms to which they are attached form a carbocyclic or heterocyclic ring having 5 or 6 ring atoms, any heteroatom being selected from N, O or S, said carbocyclic or heterocyclic ring being saturated or unsaturated, and being unsubstituted or substituted with one or more substituents selected from Cl, Br, F, OH, $NO_2$, $CF_3$, $C_{1-6}$ lower alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined above.

Compounds described above, wherein $R_2$ and $R_3$ taken together with the carbon atoms to which they are attached form a ring, may be represented by Formula (IA):

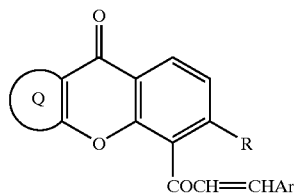

(IA)

wherein the substituents R and Ar are as defined above, and $R^2$ and $R^3$ taken together represent Ring Q, said Ring Q being a five- or six-membered, preferably aromatic, carbocyclic or heterocyclic ring, any heteroatom being selected from N, O, or S, said ring being unsaturated or saturated, said carbocyclic ring or heterocyclic ring may be unsubstituted or substituted with one or more substituents selected from: Cl, Br, F, OH, $NO_2$, $CF_3$, $C_{1-4}$ lower alkyl, $SCH_3$, $NHCOCH_3$, $N(R^6)(R^8)$, $OR^{10}$ and $OCOR^{11}$, wherein $R^8$, $R^8$, $R^{10}$ and $R^{11}$ are as defined for Formula (I).

Compounds of the invention having a structure Formula (IA) represent the xanthone derivatives of the present invention.

The present invention also embraces compounds of Formula (I), wherein R and Ar are as defined for Formula (I) above and wherein $R^2$ and $R^3$ are each independently selected from:

(i) a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of Cl, Br, F. OH, $NO_2$, $CF_3$, $C_{1-4}$, lower alkyl (in particular $CH_3$), $SCH_3$, $NHCOCH_3$, $N(R^6)(R^8)$, $OR^{10}$ and $OCOR^{11}$, wherein $R^6$, $R^8$. $R^{10}$ and $R^{11}$ are as defined above, (ii) Cl, (iii) Br, (iv) F. (v) OH, (vi) $NO_2$, (vii) a saturated or unsaturated lower $C_{1-6}$ straight or branched hydrocarbyl group which may be unsubstituted or substituted by 1, 2 or 3 substituents selected from Cl, Br, F, OMe, $NO_2$ and $CF_3$, (viii) $NHCOCH_3$, (ix) $N(R^6)(R^8)$, (x) $SR^{10}$, (xi) $OR^{10}$, and (xii) $OCOR^{11}$ wherein $R^6$, $R^8$, $R^{10}$ and $R^{11}$ are as defined above.

Such compounds include flavone derivatives according to the present invention. One preferred class of compounds according to Formula (I) are those wherein Ar, R and $R^3$ are as defined in the above paragraph and wherein $R^2$ represents a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined as for Formula (I) above, represent flavone derivatives according to the present invention.

Preferably for the above described compounds, $R^3$ is selected from the group consisting of Cl, Br, F, OH, $NO_2$, a saturated or unsaturated lower $C_{1-6}$ straight or branched hydrocarbyl group which may be unsubstituted or substituted by 1, 2 or 3 substituents selected from:

Cl, Br, F, OMe, $NO_2$ and $CF_3$;
$NHCOCH_3$, $N(R^6)(R^8)$, $SR^{10}$, $OR^{10}$ and $OCOR^{11}$, wherein $R^6$, $R^8$, ($R^{10}$ and $R^{11}$ are as defined for Formula (I) above.

In a further preferred group of compounds according to the present invention, $R^2$ represents:

a substituted or unsubstituted, preferably aromatic, carbocyclic or heterocyclic group containing from 5 to 10 ring atoms, said ring atoms forming one or two rings, wherein the or each ring contains 5 or 6 ring atoms, any heteroatoms being selected from N, O and S, any substituents being independently selected from the group consisting of:

Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined in claim 1; and $R^3$ is selected from the group consisting of Cl, Br, F, OH, $NO_2$, a saturated or unsaturated lower $C_{1-6}$ straight or branched hydrocarbyl group which may be unsubstituted or substituted by 1, 2 or 3 substituents selected from:

Cl, Br, F, OMe, $NO_2$ and $CF_3$, $NHCOCH_3$, $N(R^6)(R^8)$, $SR^{10}$, $OR^{10}$ and $OCOR^{11}$, wherein $R^6$, $R^8$, $R^{10}$ and $R^{11}$ are as defined above.

A further preferred group of compounds according to the present invention include compounds wherein $R^3$ is selected from:

Cl, Br, F, OH, $NO_2$, $CF_3$, $C_{1-4}$ lower alkyl, $SCH_3$, $NHCOCH_3$, $N(R^6)(R^8)$, $OR^{10}$, and $OCOR^{11}$ wherein $R^6$, $R^8$, $R^{10}$ and $R^{11}$ are as defined for Formula (I) above.

A particularly preferred $R^3$ group is $C_{1-4}$ lower alkyl, especially methyl.

In a further preferred class of compounds, $R^2$ preferably represents a substituted or unsubstituted (preferably aromatic) carbocyclic group containing from 5 to 10 ring atoms, said ring atoms forming one or two rings, wherein the or each ring contains 5 or 6 ring atoms, and any substituents are independently selected from the group consisting of Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined above.

Of these, $R^2$ preferably represents an unsubstituted, preferably aromatic, carbocyclic group containing from 5 to 10 ring atoms, said ring atoms forming one or two rings. An especially preferred $R^2$ group is phenyl.

For the compounds of Formula (I), Ar preferably represents phenyl which may be unsubstituted or substituted with one or more substituents selected from the group consisting of Cl, Br, F, OH, $NO_2$, $CF_3$, $C_{1-4}$ lower alkyl (in particular $CH_3$), $SCH_3$, $NHCOCH_3$, $N(R^6)(R^8)$, $OR^{10}$ and $OCOR^{11}$ wherein $R^6$, $R^8$, $R^{10}$ and $R^{11}$ are as defined for Formula (I).

Particularly preferred Ar groups include phenyl or phenyl substituted with 1, 2 or 3 methoxy groups.

For the Ar, $R^2$ and $R^3$ groups of Formula (I), the $R^{10}$ and $R^{11}$ groups are preferably a saturated or unsaturated $C_{1-6}$ a straight chain or branched hydrocarbyl group. Particularly preferred groups include methyl, ethyl, n-propyl and iso-propyl. An especially preferred group is methyl.

The group R of the compounds of the invention preferably represents the group $OR^{10}$. Within this group of compounds, preferred $OR^{10}$ groups include —$OCH_2CH$=$CMe_2$,—$OCH_2CMe$=$CH_2$, —$OCH_2CH$=$CH_2$ and —$OCH_2C$≡$CH$.

A further preferred group of compounds of the invention are compounds of Formula (I) wherein
Ar represents
phenyl, which may be unsubstituted or substituted by one, two or three substituents independently selected from Cl, Br, F, OMe, $NO_2$, $CF_3$, $C_{1-4}$ lower alkyl (in particular $CH_3$), $NMe_2$, $NEt_2$, $SCH_3$ and $NHCOCH_3$;
thienyl, 2-furyl, 3-pyridyl, 4pyridyl or indolyl; and
R represents
OH or $OCH_2R^1$, wherein $R^1$ is selected from —$CH$=$CMe_2$, —$CMe$=$CH_2$, —$CH$=$CH_2$ and —$C$≡$CH$.

Within this group of compounds, Ar is preferably selected from trimethoxyphenyl, 3-pyridyl, 4pyridyl and 3indolyl, and R is preferably selected from $OCH_2CH$=$CMe_2$, $OCH_2CMe$=$CH_2$, $OCH_2CH$=$CH_2$ and $OCH_2C$≡$CH$.

In a preferred class of compounds, Ar contains a basic nitrogen function, for example, by virtue of a heterocyclic nitrogen ring atom being present, or Ar may contain a substituent having a basic nitrogen, such as an amine, or an acetamido function. Thus a preferred Ar group is a substituted or unsubstituted, preferably aromatic, heterocyclic group, said heterocyclic group containing from 5 to 10 ring atoms, at least one of which is a nitrogen atom, said ring atoms forming one or two rings, with the or each ring containing 5 or 6 ring atoms, wherein any substituent on the ring is as defined as for Formula (I). A further preferred group of compounds is wherein the group Ar is substituted with at least one substituent selected from $NHCOCH_3$ or $N(R^6)(R^8)$, wherein $R^6$ and $R^8$ are the same or different and each represents H or lower $C_{1-4}$ alkyl.

Particularly preferred Ar groups containing a basic nitrogen function include of 3-pyridyl, 4-pyridyl, 3-indolyl, 4-dimethylaminophenyl and 4-acetamidophenyl.

It will be appreciated that compounds of Formula (I) which contain a basic amino function may be converted to acid addition salts, with pharmacologically acceptable acids, e.g. hydrochloric acid and phosphoric acid. Such salts are also included in the present invention.

The present invention also provides the use of a compound of Formula (I) in the manufacture of an antiproliferative medicament In particular, the compounds of the present invention may be useful for the manufacture of a medicament for the treatment or prevention of neoplasms, particularly those located in the uterus, ovary or breast In particular, the compounds may be useful for the manufacture of a medicament for the treatment of cancer cells that are resistant to paclitaxel and docetaxel.

The compounds of Formula (I) may advantageously be used in combination therapies involving the combined use of a compound of Formula (I) and another anti-neoplastic agent, especially paclitaxel or docetaxel. The combination therapy may involve simultaneous or successive administration of a compound of Formula (I) and an anti-neoplastic agent Such combination therapy forms a further aspect of the invention.

The compounds of the invention may be further used in the manufacture of a medicament for the treatment or prevention of menopausal disorders and osteoporosis.

The present invention further includes a pharmaceutical composition comprising one of more of the compounds of Formula I in combination with one or more pharmaceutically acceptable excipients.

DETAILED DESCRIPTION OF THE PREFERRED EMBODIMENTS

The invention will now be described by way of illustrative examples and with reference to the accompanying formulae drawings.

EXAMPLES

Example 1

General Conditions to Obtain Chalcones.
Method A.

A solution of KOH 50% (3 ml) is added to an equimolar solution of acetophenone (0.0075 mol) and aldehyde (0.0075 mol) in ethanol 95%; the addition is performed under energetic stirring at room temperature. The reaction is left under stirring for one night and then diluted with water and acidified; the precipitate is separated by filtration and dried under vacuum. The compounds are crystallized by ethanol or first separated by chromatography and then crystallized by ethanol.
Method B.

A solution of acetophenone (0.0075 mol), aldehyde (0.0075 mol), piperidine (15 ml) and acetic acid (75 ml) in ethyl alcohol 95% (80 ml) is countercurrent heated for 5 hours. Molecular sieves are added to the solution to eliminate water and the whole is left at rest for one night The precipitate that is generally obtained is gathered and crystallized. If the product does not precipitate in these conditions, the solvent is vacuum evaporated and the residue is purified by chromatography on silica gel column.

Example 2

1-[3-(3-Methylbut-2-Enyloxy)Xanthen-9-one-4-yl]-3-Phenyl-Propen-1-one (See Accompanying Formula Drawing VIB 176).

A solution of KOH 50% (3 ml) is added to an equimolar solution of 3-(3-methylbut -2-enyloxy)-4-acetylxanthen-9-one (2.4 g, 0.0075 mol) and benzaldehyde (0.8 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.1 g of product m.p. 116–118° C., $^1$H-NMR (CDCl3) δ:1.69 (s, 3H); 1.72 (s, 3H); 4.71 (d, 2H, J=6.5); 5.38–5.40 (m, 1H); 7.05–7.10 (m, 2H); 7.08 (d, 1H, J=8.8 Hz); 7.10 (d, 1H, J=16 Hz); 7.30–7.48 (m, 6H); 7.50–7.58 (m, 2H); 7.65–7.60 (m, 1 H) 8.30–8.33(m, 1H); 8.42 (d, 1H, J=8.9 Hz).

Example 3

1-[3-(3-Methylbut-2-Enyloxy)Xanthen-9-one-4-yl]-3-(3-Methoxy-Phenyl)-Propen-1-one (See Accompanying Formula drawing VIB 177).

A solution of KOH 50% (3 ml) is added to an equimolar solution of 3-(3-methylbut -2-enyloxy)4acetylxanthen-9one (2.4 g, 0.0075 mol) and 3-methoxy-benzaldehyde (1.01 g, 0.0075 mol) in ethanol 95%, the addition being performed under energetic stirring at room temperature. The reaction is left under stirring for one night and then diluted with water and acidified. The precipitate is separated by filtration and dried under vacuum. The compound is crystallized with methanol to give 1.9 g of product m.p. 134–36° C., $^1$H-NMR (CDCl$_3$) δ: 1.69 (s, 3H); 1.72 (s, 3H); 3.84 (s, 3H); 4.71 (d, 2H, J=6.5); 5.38–5.40 (m, 1H); 6.95–6.98 (m, 1H); 7.05–7.15 (m, 2H); 7.08 (d, 1H, J=8.8 Hz); 7.09 (d, 1H, J=16 Hz); 7.23–7.42 (m, 4H); 7.65–7.72 (m, 1H); 8.32–8 (d, 1H. J=8.8 Hz); 8.42(d, 1H. J=8.9 Hz).

Example 4

1-[3-(3-Methylbut-2-Enyloxy)Xanthen-9-one-4-yl]-3-(3,4,5-Tri-Methoxyphenyl)-Propen -1-one (See Accompanying Formula drawing VIB 178).

A solution of KOH 50% (3 ml) is added to an equimolar solution of 3-(3-methylbut -2-enyloxy)-4-acetylxanthen-9-one (2.4 g, 0.0075 mol) and 3, 4, 5-trimethoxy-benzaldehyde (1.47 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.2 g of product m.p. 153–55° C., $^1$H NMR (CDCl$_3$) δ:1.69 (s, 3H); 1.72 (s, 3H); 3.85–3.91 (m, 9H); 4.73 (d, 2H, J=6.5); 5.38–5.40 (m, 1H); 6.78 (s, 2H); 7.03 (d, 1H, J=16 Hz); 7.09 (d, 1H, J=8.8 Hz); 7.23–7.42 (m, 2H); 7.27 (d, 1H J=16 Hz); 7.80–7.87; (m, 1H); 8.32 (d, 1H, J=8.8 Hz); 8.44 (d, 1H, J=8.9 Hz).

Example 5

1-[3-(Allyloxy)Xanthen-9-one-4-yl]-3-Phenyl-Propen-1-one (See Accompanying Formula Drawing VIB 175).

A solution of KOH 50% (3 ml) is added to an equimolar solution of 3-allyloxy-4-acetylxanthen -9one (2.2 g, 0.0075 mol) and benzaldehyde (0.8 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2 g of product m.p. 150–152° C., $^1$H-NMR (CDCl$_3$)δ:4.73–4.74 (m, 2H); 5.25–5.42 (m, 2H); 5.92–6.05 (m, 1H); 7.07 (d, 1H, J=8.9 Hz); 7.13 (d, 1H, J=16 Hz); 7.36–7.44 (m, 6H); 7.52–7.60 (m, 2H); 8;31–8.36 (m, 1H); 8.43 (d, 1 H, J=8.9 Hz).

Example 6

1-[3-Methyl-7-(3-Methylbut-2-Enyloxy)Flavon-8-yl]-3-Phenyl-Propen -1-one (See Accompanying Formula Drawing VIB 166).

A solution of KOH 50% (3 ml) is added to an equimolar solution of 7-(3-methylbut -2-enyloxy)-8-acetyl-3-methylflavone (2.71 g, 0.0075 mol) and benzaldehyde (0.8 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.3 g of product m.p. 83–84° C., $^1$H-NMR (CDCl$_3$)δ:1.67 (s, 3H); 1.70 (s, 3H); 2.18 (5, 3H); 4.68 (d, 2H, J=6.4 Hz); 5.30–5.38 (m, 11H); 7.00 (d, 1H, J=16 Hz); 7.02 (d, 11, J=8.9 Hz; 7.24 (d, 1H, J=16 Hz); 7.30–7.45 (m, 6H); 7.48–7.54 (m, 4H);8.30 (d, 1H, J=8.9 Hz).

Example 7

1-[3-Methyl-7-(3-Methylbut-2-Enyloxy)Flavon-8-yl]-3-(3-Methoxy)Phenyl-Propen -1-one (See Accompanying Formula Drawing VIB 170).

A solution of KOH 50% (3 ml) is added to an equimolar solution of 7-(3-methylbut -2enyloxy)acetyl-3methylflavone (2.71 g, 0.0075 mol) and 3 methoxy-benzaldehyde (1.01 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.2 g of product m.p. 134–136° C., $^1$H-NMR (CDCl3)δ:1.67 (s, 3H); 1.70 (s, 3H); 2.18 (s, 3H); 3.82 (s, 3H) 4.68 (d, 2H, J=6.4 Hz); 5.30–5.38 (m, 1H);6.93 (d, 1H, J=16 Hz,); 6.96–7;18 (m, 3H);7.09 (d, 1H, J=8,9 Hz); 7.20 (d, 1H, J=16 Hz) 7.23–7.30 (m, 1H); 7.35–7.45 (m, 3H); 8.30 (d, 1H, J=8.9Hz).

Example 8

1-[3-Methyl-7-(3-Methylbut-2-Enyloxy)Flavon-8-yl]-3-(3,4,5-Tri-Methoxy)Phenyl-Propen -1-one (See Accompanying Formula Drawing VIB 173).

A solution of KOH 50% (3 ml) is added to an equimolar solution of 7-(3-methylbut -2-enyloxy)8acetyl-3-methylflavone (2.71 g, 0.0075 mol) and 3,4,5trimethoxy-benzaldehyde (1.47 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2 g of product m.p. 153–55° C, $^1$H-NMR (CDCl$_3$) δ:1.70 (s, 3H); 1.72 (s, 3H); 2.18 (s, 3H); 3.86–3.91 (m, 9H); 4.70 (d, 2H, J=6.4 Hz); 5.34–5.42 (m, 1H); 6.73 (s, 2H); 6.93 (d, 1H, J=16 Hz); 7.09 (d, 1H, J=8.9 Hz); 7.22 (d, 1H, J=16 Hz); 6.96–7.18 (m, 3H); 7.52–7.58 (m, 2H); 8.32 (d, 1H, J=8.9 Hz).

Example 9

1-[3-Methyl-7-(Allyloxy)Flavon-8-yl]-3-Phenyl-Propen-1-one (See Accompanying Formula Drawing VIB 164).

A solution of KOH 50% (3 ml) is added to an equimolar solution of 7-allyloxy-8-acetyl -3-methylflavone (2.5 g, 0.0075 mol) and benzaldehyde (0.8 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.3 g of product m.p. 145–47° C., $^1$H-NMR (CDCl3) δ:1.77 (s, 3H); 2.20 (s, 3H); 4.73 (d, 2H, J=5.1 Hz); 5.25–5.45 (m, 2H); 5.91–6.02 (m, 1 H); 7.05 (d, 1H, J=16 Hz); 7.11 (d, 1H, J=8.9 Hz); 7.38–7.48 (m, 7H); 7.53–7.59 (m, 4H); 8.34 (d, 1H, J=8.9 Hz).

Example 10

1-[3-Methyl-7-(Allyloxy)Flavon-8-yl)-3-(3-Methoxyphenyl)-Propen -1-one (See Accompanying Formula Drawing VIB 168).

A solution of KOH 50% (3 ml) is added to an equimolar solution of 7-allyloxy-8acetyl -3-methylflavone (2.5 g, 0.0075 mol) and 3-methoxy-benzaldehyde (1.01 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.4 g of product m.p. 90–92° C., $^1$H-NMR (CDCl$_3$)

δ:2.20 (s, 3H); 3.84 (s, 3H); 4.74 (d, 2H, J=5.1 Hz); 5.1–5.3 (m, 2H); 5.91–6.02 (m, 1H); 6.96–7.18 (m, 4H); 7.31 (d, 1H, J=16 Hz); 7.32–7.35 (m, 1H); 7.36–7.43 (m, 3H); 7.55–7.59 (m, 2H); 8.34 (d, 1H, J=8.9Hz).

Example 11

1-[3-Methyl-7-(Allyloxy)Flavon-8-yl]-3-(3,4,5-Trimethoxy-Phenyl)Propen -1-one (See Accompanying Formula Drawing VIB 171).

A solution of KOH 50% (3 ml) is added to an equimolar solution of 7-allyloxy-8-acetyl -3methylflavone (2.5 g, 0.0075 mol) and 3,4,5-trimethoxy-benzaldehyde (1.47 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.4 g of product m.p. 121–23° C., $^1$H-NMR (CDCl$_3$)δ: 2.20 (s, 3H); 3.87 (m, 9H); 4.73 (d, 2H, J=5,1 Hz; 5.25–5.45 (m, 2H); 5.91–6.02 (m, 1H); 6.75 (s, 2H); 6.96 (d,1H, J=16 Hz); 7.10 (d, 1H, J=8.9 Hz); 7.30 (d, 1H, J=16 Hz); 7.42–7.46 (m, 3H); 7.55–7.59 (m, 2H); 8.34 (d, 1H, J=8.9 Hz).

Example 12

1-[3-Methyl-7-(2-Methylallyloxy)Flavon-8-yl]-3-Phenylpropen-1-one (See Accompanying Formula Drawing VIB 165).

A solution of KOH 50% (3 ml) is added to an equimolar solution of 7-(2-methylallyloxy) 8acetyl-3methylflavone (2.61 g, 0.0075 mol) and benzaldehyde (0.8 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.8 g of product m.p. 145–47° C., $^1$H-NMR (CDCl$_3$) δ:1.78 (s, 3H); 2.20 (s, 3H); 4.62 (s, 2H); 4.98 (d, 2H, J=18 Hz); 7.06 (d,1H, J=16 Hz); 7.09 (d, 1H, J=8.9 Hz); 7.35–7.45 (m,7H); 7.50–7.55(m, 4H); 8.32 (d, 1H, J=8.9 Hz).

Example 13

1-[3-Methyl-7-(2-Methylallyloxy)flavon-8-yl]-3-(3-Methoxy-Phenyl)-Propen-1-one (See Accompanying Formula Drawing VIB 169).

A solution of KOH 50% (3 ml) is added to an equimolar solution of 7-(2-methylallyloxy) -acetyl-3methylflavone (2.61 g, 0.0075 mol) and 3-methoxy-benzaldehyde (1.01 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.4 g of product m.p. 131–34° C., $^1$H-NMR (CDCl$_3$) δ:1.76 (s, 3H); 2.20 (s, 3H); 3.82 (s, 3H) 4.62 (s, 2H); 5.05 (d, 2H, J=18 Hz); 6.95–7.10 (m, 3H); 7.09 (d, 1H, J=9 Hz); 7.10 (d, 1H, J=9 Hz); 7.31 (d, 1H, J=16 Hz); 7.40–07.45 (m, 3H); 7.55–7.58 (m, 2H); 7.31 (s, 2H); 8.32 (d, 1H, J=8.9 Hz).

Example 14

1-[3-Methyl-7-(2-Methylallyloxy)Flavon-8-yl]-3-(3,4,5-Tri-Methoxyphenyl)-Propen-1-one (See Accompanying Formula Drawing VIB 172).

A solution of KOH 50% (3 ml) is added to an equimolar solution of 7-(2-methylallyloxy)-8-acetyl-3-methylflavone (2.61 g, 0.0075 mol) and 3,4,5-trimethoxy-benzaldehyde (1.47 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.4 g of product m.p. 82–84° C., $^1$H-NMR (CDCl$_3$) δ:1.76 (s, 3H); 2.20 (s, 3H); 3.82 (s, 3H); 4.62 (s, 2H); 5.05 (d, 2H, J=18 Hz); 6.95–7.10 (m, 3H); 7.09 (d, $_1$H); 7.10 (d, 1H, J=9 Hz); 7.31 (d, 1H, J=16 Hz); 7.40–7.45 (m, 3H); 7.55–7.58 (m, 2H); 7.31 (s, 2H); 8.32 (d, 1H, J=8.9 Hz).

Example 15

1-[3-Methyl-7-(Prop-2-ynyloxy)flavon-8-yl]-Phenyl-Propen-1-one (See Accompanying Formula Drawing VIB 167).

A solution of KOH 50% (3 ml) is added to an equimolar solution of 7-(prop-2-ynyloxy) -8-acetyl-3-methylflavone (2.49 g, 0.0075 mol) and benzaldehyde (0.8 g, 0.0075 mol) in ethanol 95%. The addition is performed under energetic stirring at room temperature. The reaction is left under stirring for one night and then diluted with water and acidified; the precipitate is separated by filtration and dried under vacuum. The compound is crystallized by methanol to give 2.8 g of product m.p. 157–59° C., $^1$H-NMR (CDCl$_3$)δ: 2.20 (s, 3H); 2.56 (s, 1H); 4.86 (d, 2H, J=2.2 Hz); 7.05 (d, 1H, J=16 Hz); 7.23 (d, 1H, J=8.9 Hz); 7.31–7.50 (m, 7H); 7.50–7.57 (m, H); 8,34 (d, 1H, J=8.9 Hz).

Example 16

1-[3-Methyl-7Prop-2-ynyloxy)flavon-8-yl]-3-(3,4,5~Trimethoxy-Phenyl)Propen-1-one (See Accompanying Formula Drawing VIB 174).

A solution of KOH 50% (3 ml) is added to an equimolar solution of 7-(prop-2-ynyloxy) -8-acetyl-3-methylflavone (2.49 g, 0.0075 mol) and 3,4,5trimethoxy-benzaldehyde (1.47g, 0.0075 mol) in ethanol 95%. The addition is performed under energetic stirring at room temperature. The reaction is left under stirring for one night and then diluted with water and acidified; the precipitate is separated by filtration and dried under vacuum. The compound is crystallized by methanol to give 2.8 g of product m.p. 152–54° C., $^1$H-NMR (CDCl$_3$)δ: 2.02 (s, 3H), 2.56 (m, 1H); 3.86 (m, 9H); 4.86 (d, 2H, J=2.2 Hz); 6.75 (s, 2H); 6.98 (d, 1H, J=16 Hz); 7.24–7.43 (m, 4H); 7.53–7.56 (m, 3H); 8.36 (d, 1H, J=8.9 Hz).

Example 17

1-[3-Methyl-7-(3-Methylbut-2-Enyloxy)Flavon-8-yl]-3-(2-Thienyl)-Propen -1-one (See Accompanying Formula Drawing VIB 238).

A solution of KOH 50% (3 ml) is added to an equimolar solution of 7-(3-methylbut -2enyloxy)-8-acetyl-3-methylflavone (2.71g, 0.0075 mol) and 2-thiophene-carboxyaldehyde (0.84 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.5 g of product m.p. 158–160° C., $^1$H-NMR (CDCl$_3$)δ: 1.58 (s, 3H), 2.07 (s, 3H), 4.6 (d, J=6.6 Hz, 2H), 5.3 (m, 1H), 6.65–818 (m, 12H).

Example 18

1-[3-Methyl-7-Methoxyflavon-8-yl]-3-(4Cyanophenyl)-Propen -1-one (see accompanying formula drawing VIB 247).

A solution of KOH 50% (3 ml) is added to an equimolar solution of 7-methoxy -8-acetyl-3methylflavone (2.31 g, 0.0075 mol) and 4-cyanobenzaldehyde (0.98 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by ethanol to give 2.1 g of product m.p. 223–224C, $^1$H-NMR (CDCl$_3$) δ:2.18 (s, 3H), 3.96 (s, 3H), 7.04–8.36 (m, 13H).

Example 19

1-(2-Methylallyloxy-Xanthen-9-one-4yl)-3-(4-Fluorophenyl)-Propen -1-one (See Accompanying Formula Drawing VIB 245).

A solution of KOH 50% (3 ml) is added to an equimolar solution of 3-(2-1 methylallyloxy)-4-acetyl-xanthen-9one (2.31 g, 0.0075 mol) and 4-fluoro-benzaldehyde (0.93 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.2 g of product m.p. 135–137° C., $^1$H-NMR (CDCl$_3$) δ:1.7 (m, 3H), 4.5 (m, 2H), 4.98 (m, 2H), 7.0–8.45 (m, 12H).

Example 20

1-(2-Allyloxy-Xanthen-9-one-4-yl)-3-(4-Methylthiophenyl)Propen -1-one (See Accompanying Formula Drawing VIB 244).

A solution of KOH 50% (3 ml) is added to an equimolar solution of 3allyloxy) -4-acetylxanthen-9-one (2.21 g, 0.0075 mol) and 4methylthio-benzaldehyde (1.13 g, 0.0075 mol) in ethanol 95%; the addition is performed under energetic stirring at room temperature. The reaction is left stirring for one night and then diluted with water and acidified; the precipitate is separated by filtration and dried under vacuum. The compound is crystallized by methanol to give 2.1 g of product m.p. 142–144° C., $^1$H-NMR (CDCl$_3$)δ: 2.49 (s, 3H), 4.7 (d, 2H), 5.3 (m, 2H), 5.9 (m, 1H), 7.03–8.41 (m, 12H).

Example 21

1-[3-Methyl-7-(3-Methylbut-2-Enyloxy)Flavon-8-yl]-3-(4-Chloro-Phenyl)-Propen-1-one (See Accompanying Formula Drawing VIB 239).

A solution of KOH 50% (3 ml) is added to an equimolar solution of 7-(3-methylbut-2-enyloxy)-8-acetyl-3-methylflavone (2.71 g, 0.0075 mol) and 4-chloro-benzaldehyde (1.05 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 1.9 g product m.p. 130–133° C., $^1$H-NMR (CDCl$_3$) δ:1.69 (s, 3H), 1.72 (s, 3H), 2.19 (s, 3H), 4.65 (d. 2H), 5.31 (m, 1H), 6.97–8.42 (m, 13H).

Example 22

1-(2Methylallyloxy-Xanthen-9-one-4yl)-3-(2,6-Dichloro-Phenyl)-Propen -1-one (See Accompanying Formula Drawing VIB 246).

A solution of KOH 50% (3 ml) is added to an equimolar solution of 3-(2-methylallyloxy -4acetyl-xanthen-9-one (2.31 g, 0.0075 mol) and 2,6dichloro-benzaldehyde (1.31 g, 0.0075 mol) in ethanol 95%; the addition is performed under energetic stirring at room temperature. The reaction is left under stirring for one night and then diluted with water and acidified; the precipitate is separated by filtration and dried under vacuum. The compound is crystallized by methanol to give 2.1 g of product m.p. 135–137° C., $^1$H-NMR (CDCl$_3$) δ:4.74 (m, 2H), 5.4 (m, 2H), 5.95 (m, 1H), 7.06–8.5 (m, 11 H).

Biological Evaluation

Compounds VIB 167, VIB 178 and VIB 173 were tested for their cytotoxicity against drug-resistant cancer cells, both alone, and in combination with paclitaxel. The results of these studies are shown below.

When tested alone, compounds VIB 167, VIB 178 and VIB 173 were found to possess relatively low cytotoxicity ($IC_{50}$>1 μM) against drug-resistant cancer cells.

The compounds were then evaluated in combination with paclitaxel for their cytostatic activity against the drug-resistant breast cancer cells MDA-435/LCC6-MDR.

In the experiments, the compounds were used in combination with paclitaxel, the paclitaxel being at a concentration of 0.3 μM. Paclitaxel used alone possesses an $IC_{50}$ of 426 nM. However, as the results in Table 1 indicate, the $IC_{50}$ of paclitaxel decreases by 5–20 fold when used in combination with each of VIB 167, VIB 178 and VIB 173., i.e. from 426 nM to 82–21 nM, compared with paditaxel alone. Consequently, in the presence of these compounds, paclitaxel can recover its excellent inhibitory activity against the drug-resistant cancer cells.

TABLE 1

| Compound | $IC_{50}$/nM | % Reduction in $IC_{50}$ of paclitaxel |
|---|---|---|
| Paclitaxel | 426 | — |
| VIB 167 + Paclitaxel | 82 | 80 |
| VIB 178 + Paclitaxel | 50 | 88 |
| VIB 173 + Paclitaxel | 21 | 95 |

Experimental

The treatment consisted of concurrent exposure of MDA-435/LCC-MDR cells to paclitaxel in the presence or absence of the compounds reversing agent (1 μM) for 72 h in vitro. Assessment of cytotoxicity, i.e. cell growth inhibition, was determined according to the methods of Skehan, et al. as discussed in J. Nat. Cancer Inst, 82, 1107, 1990.

Briefly, cells were plated between 400 and 1200 cells/well in 96 well plates and incubated at 37° C. for 15–18 h prior to drug addiction to allow attachment of cells. Compounds were solubilized in 100% DMSO and further diluted in RPMI-1640 containing 10 mM HEPES. After a 72 h incubation, 100 μl of ice-cold 50% TCA was added to each well and incubated for 1 h at 40° C. Plates were then washed 5 times with tap water to remove TCA, low-molecular weight metabolites and serum proteins. Suforhodamine B (SRB) (0.4%, 50 μl) was added to each well. Following a five minute incubation at room temperature, plates were rinsed 5 times with 0.1% acetic acid and air dried. Bound dye was solubilized with 10 mM Tris Base (pH 10.5) for 5 mm on a gyratory shaker. Optical density was measured at 570 nm.

VIB 176
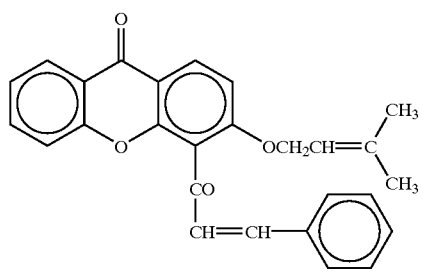
VIB 170
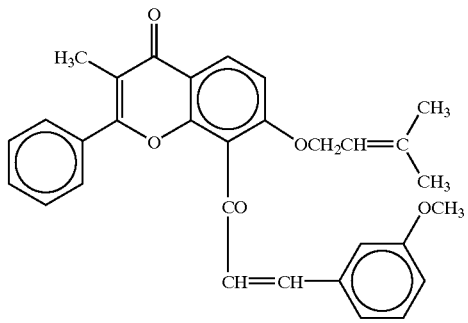
VIB 177
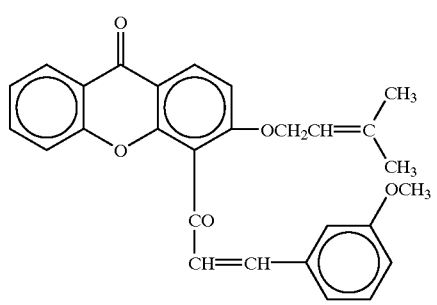
VIB 173
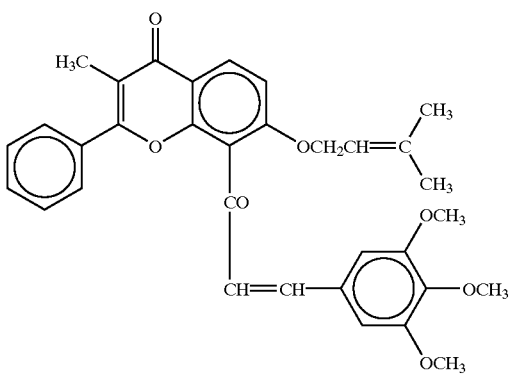
VIB 178
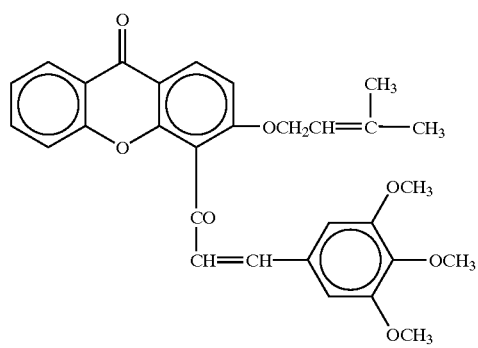
VIB 164
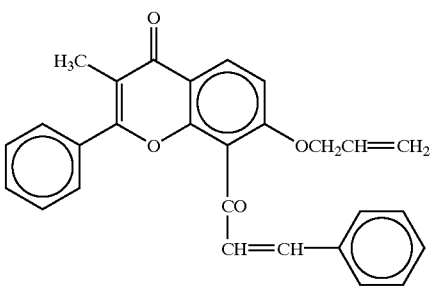
VIB 175
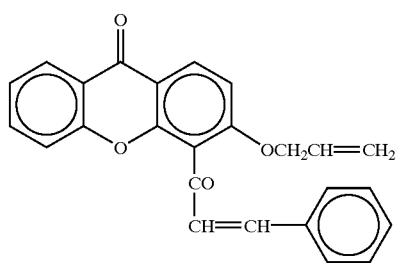
VIB 168
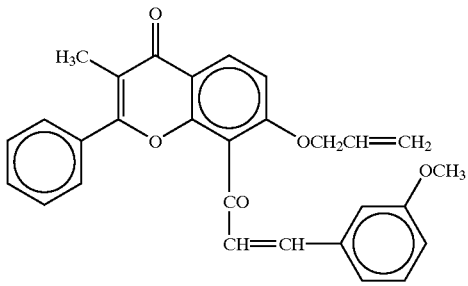
VIB 166
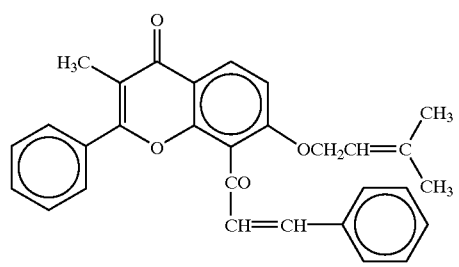
VIB 171
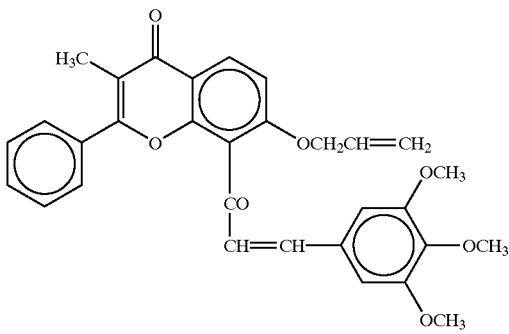

-continued
VIB 165
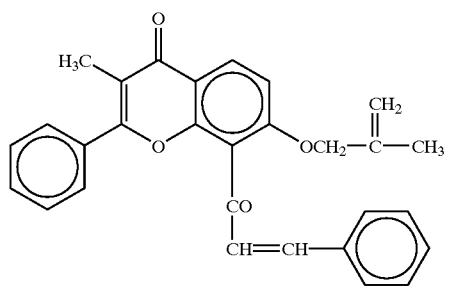
VIB 169
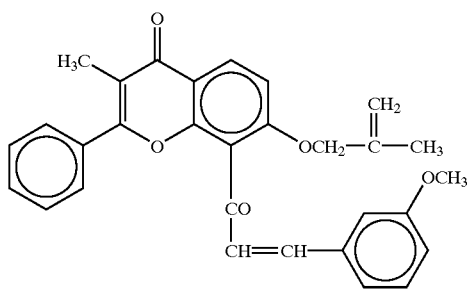
VIB 172
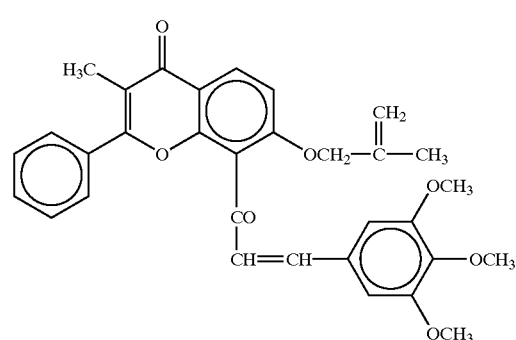
VIB 167
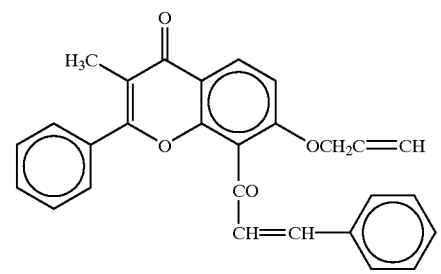
VIB 174
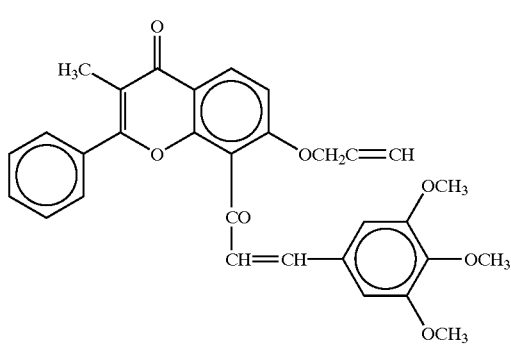
-continued
VIB 238
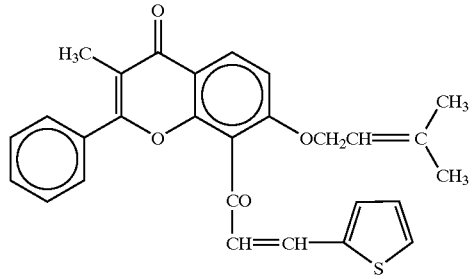
VIB 239
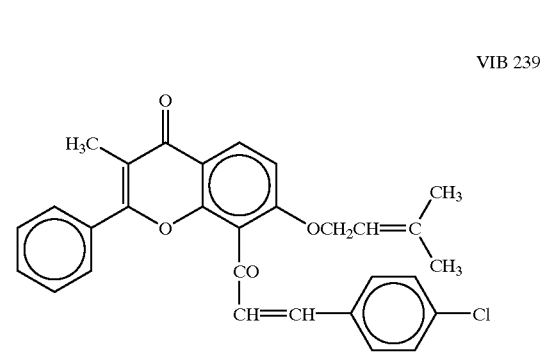
VIB 247
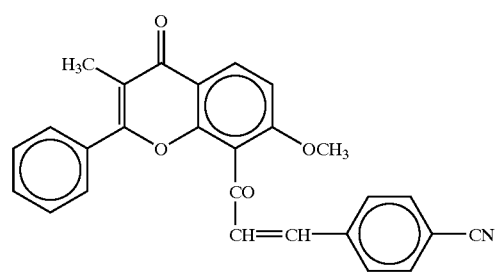
VIB 244
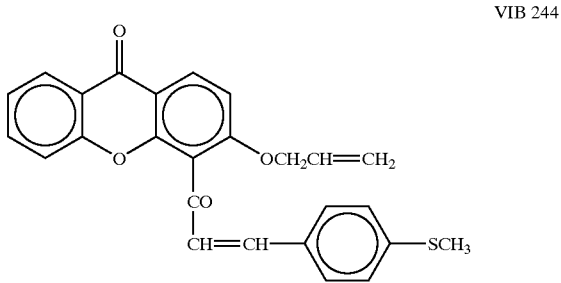
VIB 245
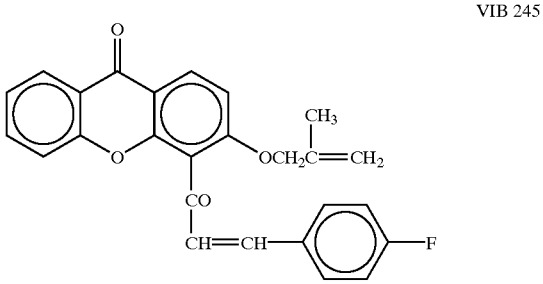

-continued

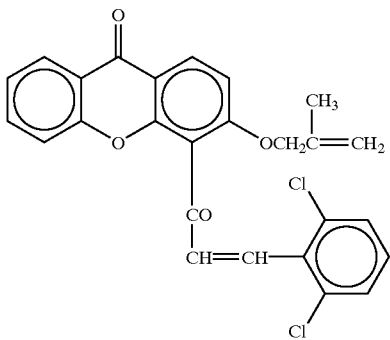

VIB 246

What is claimed is:

1. A compound of Formula (I):

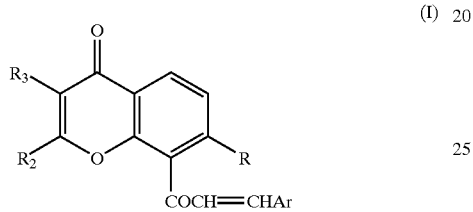

(I)

or a pharmaceutically acceptable salt or solvate thereof wherein:

Ar represents an aromatic or non-aromatic, carbocyclic or heterocyclic group having from 5 to 10 ring atoms or two rings with each ring containing 5 or 6 ring atoms, wherein the heterocyclic group comprises a heteroatom selected from N, O and S, and wherein the carbocyclic or heterocyclic group may be unsubstituted or substituted with one or more substituents selected from: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$, wherein $R^6$ and $R^8$ are the same or different and each represents H or $C_{1-4}$ alkyl, (k) $OR^{10}$ wherein $R^{10}$ represents a saturated or unsaturated $C_{1-6}$ straight or branched hydrocarbyl group which may be unsubstituted or substituted with from 1 to 3 substituents selected from: Cl, Br, F, OMe, $NO_2$, and $CF_3$, and (1) —$OCOR^{11}$, wherein $R^{11}$ represents a saturated or unsaturated $C_{1-6}$ straight or branched hydrocarbyl group or a phenyl group;

R represents OH, $OR^{10}$ or $OCOR^{11}$, $R^{10}$ and $R^{11}$ are as defined above; and (A) $R^2$ $R^3$ are each independently selected from:
(i) an aromatic or non-aromatic, carbocyclic or heterocyclic group containing from 5 to 10 ring atoms or two rings with each ring containing 5 or 6 ring atoms, wherein the heterocyclic group comprises a heteroatom selected from N, O, and S, and wherein the carbocyclic or heterocyclic group may be unsubstituted or substituted with one or more substituents selected from: Cl, Br, F, OH, $NO_2$, $CF_3$, $C_{1-4}$ alkyl, $SCH_3$, $NHCOCH_3$, $N(R^6)(R^8)$, $OR^{10}$, and $OCOR^{11}$, wherein $R^6$, $R^8$, $R^{10}$ and $R^{11}$ are as defined above,
(ii) Cl;
(iii) Br;
(iv) F;
(v) OH;
(vi) $NO_2$;
(vii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
(viii) $NHCOCH_3$;
(ix) $N(R^6)(R^8)$, wherein $R^6$ is defined above;
(x) $SR^{10}$, wherein $R^{10}$ as defined above;
(xi) $OR^{10}$, wherein $R^{10}$ as defined above; and
(xii) $OCOR^{11}$, wherein $R^{11}$ is as defined above; or (B) $R_2$ and $R_3$ taken together with the carbon atoms to which they are attached form a saturated or unsaturated, carbocyclic or heterocyclic ring having 5 or 6 ring atoms, wherein the heterocyclic group comprises a heteroatom selected from N, O or S, and wherein the carbocyclic or heterocyclic group may be unsubstituted or substituted with one or more substituents selected from Cl, Br, F, OH, $NO_2$, $CF_3$, $C_{1-4}$ alkyl, $SCH_3$, $NHCOCH_8$, $N(R^6)(R^8)$, $OR^{10}$ and $OCOR^{11}$, wherein $R^6$, $R^8$, $R^{10}$ and $R^{11}$ are as defined above, with the proviso that for compounds wherein R is OH and $R^2$ and $R^3$ are both methyl, the group Ar does not represent phenyl, 4-chlorophenyl, 4-methylphenyl, 2-chlorophenyl, 3,4-dimethoxyphenyl, 4-methoxyphenyl, 4-(N,N-dimethylaminophenyl), 2-hydroxyphenyl or 2-hydroxy-1naphthyl.

2. The compound of claim 1 having the structure:

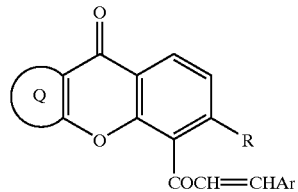

(IA)

wherein $R^2$ and $R^3$ taken together represent ring Q, wherein ring Q is a carbocyclic or heterocyclic, saturated or unsaturated ring having 5 or 6 ring atoms, wherein the heterocyclic group comprises a heteroatom selected from N, O, or S, and wherein the carbocyclic or heterocyclic group may be unsubstituted or substituted with one or more substituents selected from: Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$.

3. The compound of claim 1, wherein $R^2$ and $R^3$ are each independently selected from:
(i) an aromatic or non-aromatic, carbocyclic or heterocyclic group containing from 5 to 10 ring atoms and one or two rings each containing 5 or 6 ring atoms, wherein the heterocyclic group comprises a heteroatom selected from N, O and S, and wherein the carbocyclic or heterocyclic group may be unsubstituted or substituted with one or more substituents selected from Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$;
(ii) Cl;
(iii) Br;
(iv) F;
(v) OH;
(vi) $NO_2$;

(vii) a saturated or unsaturated $C_{1-4}$ straight or branched hydrocarbyl group which may be unsubstituted or substituted with from 1 to 3 substituents selected from Cl, Br, F, OMe, $NO_2$ and $CF_3$;

(viii) $NHCOCH_3$;

(ix) $N(R^6)(R^8)$;

(x) $SR^{10}$;

(xi) $OR^{10}$; and (xii) $OCOR^{11}$.

4. The compound of claim 3, wherein $R^2$ represents an aromatic or non-aromatic, carbocyclic or heterocyclic group containing from 5 to 10 ring atoms or two rings with each ring containing 5 or 6 ring atoms, wherein the heterocylcic group comprises a heteroatom selected from N, O and S, and wherein the carbocyclic or heterocyclic group may be unsubstituted or substituted with one or more substituents selected from Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$.

5. The compound of claim 3, wherein $R^3$ is selected from the group consisting of: Cl, Br, F, OH, $NO_2$, a saturated or unsaturated $C_{1-4}$ straight or branched hydrocarbyl group which may be unsubstituted or substituted with from 1 to 3 substituents selected from: Cl, Br, F, OMe, $NO_2$, $CF_3$, $NHCOCH_3$, $N(R^6)(R^8)$, $SR^{10}$, $OR^{10}$ and $OCOR^{11}$.

6. The compound of claim 3 wherein $R^2$ represents an aromatic or non-aromatic, carbocyclic or heterocyclic group containing from 5 to 10 ring atoms or two rings with each ring containing 5 or 6 ring atoms, wherein the heterocyclic group comprises a heteroatom selected from N, O and S, and wherein the carbocyclic or heterocyclic group may be unsubstituted or substituted with one or more substituents selected from Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$; and $R^3$ is selected from the group consisting of: Cl, Br, F, OH, $NO_2$, a saturated or unsaturated $C_{1-4}$ straight or branched hydrocarbyl group which may be unsubstituted or substituted with from 1 to 3 substituents selected from Cl, Br, F, OMe, $NO_2$, $CF_3$, NHCOCHS, $N(R^6)(R^8)$, $SR^{10}$, $OR^{10}$ and $OCOR^{11}$.

7. The compound of claim 1, wherein $R^3$ is selected from: Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$.

8. The compound according of claim 7, wherein $R^3$ is a $C_{1-4}$ alkyl group.

9. The compound of claim 8, wherein $R^3$ is methyl.

10. The compound of claim 1, wherein $R^2$ is an aromatic or non-aromatic, carbocyclic group containing from 5 to 10 ring atoms or two rings each containing 5 or 6 ring atoms, and wherein the carbocyclic or heterocyclic group may be unsubstituted or substituted with one or more substituents selected from: Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$.

11. The compound of claim 1, wherein $R^2$ is an unsubstituted, aromatic, carbocyclic group.

12. The compound of claim 1, wherein $R^2$ is phenyl.

13. The compound of claim 1, wherein $R^{10}$ and $R^{11}$ are a saturated or unsaturated $C_{1-6}$ straight chain or branched hydrocarbyl group.

14. The compound of claim 13, wherein $R^{10}$ and $R^{11}$ are selected from methyl, ethyl, n-propyl and iso-propyl.

15. The compound of claim 1, wherein R represents —$OCH_2CH$=$CMe_2$, —$OCH_2CMe$=$CH_2$, —$OCH_2CH$=$CH_2$, or —$OCH_2C$≡$CH$.

16. The compound of claim 1, wherein Ar is phenyl which may be unsubstituted or substituted with one or more substituents selected from the group consisting of Cl, Br, F, OH, $NO_2$, $CF_3$, $C_{1-4}$ alkyl, $SCH_3$, $NHCOCH_3$, $N(R^6)(R^8)$, $OR^{10}$ and $OCOR^{11}$, wherein $R^6$, $R^8$, $R^{10}$ and $R^{11}$ are as defined in claim 1.

17. The compound of claim 1, wherein Ar is phenyl or phenyl substituted with between 1 and 3 methoxy groups.

18. The compound of claim 1, wherein Ar is selected from trimethoxyphenyl, 3-pyridyl, 4-pyridyl, and 3-indolyl; and R is selected from $OCH_2CH$=$CMe_2$, $OCH_2CMe$=$CH_2$, $OCH_2CH$=$CH_2$, and $OCH_2C$≡$CH$.

19. The compound of claim 1, wherein Ar is phenyl which may be unsubstituted or substituted with from 1 to 3 substituents independently selected from Cl, Br, F, OMe, $NO_2$, $CF_3$, $C_{1-4}$ alkyl, $NMe_2$, $NEt_2$, $SCH_3$ and $NHCOCH_3$; thienyl; 2-furyl; 3-pyridyl; 4-pyridyl; and indolyl and R is OH or $OCH_2R^1$, wherein $R^1$ is selected from —CH=$CMe_2$, —CMe=$CH_2$, —CH=$CH_2$ and —C≡CH.

20. The compound of claim 1, wherein the group Ar is a substituted or unsubstituted, aromatic, heterocyclic group, containing from 5 to 10 ring atoms or two rings with each ring containing 5 or 6 ring atoms, wherein at least one of the heteroatoms is nitrogen.

21. The compound of claim 1, wherein the group Ar is substituted with at least one substituent selected from $NHCOCH_3$ or $N(R^6)(R^8)$, wherein $R^6$ and $R^8$ are the same or different and each is H or $C_{1-4}$ alkyl.

22. The compound of claim 1, wherein Ar is selected from the group consisting of 3-pyridyl, 4-pyridyl, 3-indolyl, 4-dimethyl-aminophenyl and 4-acetamidophenyl.

23. A compound of claim 1 selected from:

1-[3-(3-methylbut-2-enyloxy)xanthen-9-one-4-yl]-3-phenyl-propen-1-one,

1-[3-(3-methylbut-2-enyloxy)xanthen-9-one-4-yl]-3-methoxy-phenyl)-propen-1-one,

1-[3-(3-methylbut-2-enyloxy)xanthen-9-one-4-yl]-3-(3,4,5-tri-methoxyphenyl)-propen-1-one, 1-[3-(allyloxy)xanthen-9-one-4-yl]-3-phenyl-propen-1-one, 1-[3-methyl-7-(3-methylbut-2-enyloxy)flavon-8-yl]-3-phenyl-propen-1-one, 1-[3-methyl-7-(3-methylbut-2-enyloxy)flavon-8-yl]-3-(3-methoxy)phenyl-propen-1-one, 1-[3-methyl-7-(3-methylbut-2-enyloxy)flavon-8-y]-3-(3,4,5-trimethoxy)phenyl propen-1-one, 1-[3-methyl-7-(allyloxy)flavon-8-yl]-3-phenyl-propen-1-one, 1-[3-methyl-7-(methyl-7-(allyloxy)flavon-8-yl]-3-(3-methoxyphenyl)-propen-1-one, 1-[3-methyl-7-(allyloxy)flavon-8-yl]-3-(3,4,5-trimethoxy-phenyl)propen-1-one, 1-[3-methyl-7-(2-methylallyloxy)flavon-a-yl]-3-phenylpropen-1-one, 1-[3-methyl-7-(2-methylallyloxy)flavon-8-yl]-3-(3-methoxy-phenyl)-propen-1-one, 1-[3-methyl-7-(2-methylallyloxy)flavon-8-yl]-3-(3-methoxy-phenyl)-propen-1-one, 1-[3-methyl-7-(pro-2-ynyloxy)flavon-8-yl]-3-phenyl-propen-1-one, and 1-[3-methyl-7-(pro-2-ynyloxy)flavon-8-yl]-3-(3,4,5-trimethoxy-phenyl)-propen-1-one.

24. A method of treating cancer in a patient comprising administering to said patient a compound of Formula (I):

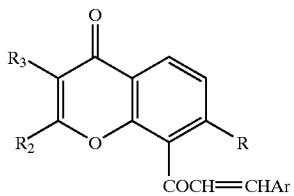

(I)

or a pharmaceutically acceptable salt or solvate thereof wherein:

Ar represents an aromatic or non-aromatic, carbocyclic or heterocyclic group having from 5 to 10 ring atoms or two rings with each ring containing 5 or 6 ring atoms, wherein the heterocyclic group comprises a heteroatom selected from N, O and S, and wherein the carbocyclic or heterocyclic group may be unsubstituted or substituted with one or more substituents selected from: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$, wherein $R^6$ and $R^8$ are the same or different and each represents H or $C_{1-4}$ alkyl, (k) $OR^{10}$, wherein $R^{10}$ represents a saturated or unsaturated $C_{1-6}$ straight or branched hydrocarbyl group which may be unsubstituted or substituted with from 1 to 3 substituents selected from: Cl, Br, F, OMe, $NO_2$, and $CF_3$, and (1) —$OCOR^{11}$, wherein $R^{11}$ represents a saturated or unsaturated $C_{1-6}$ straight or branched hydrocarbyl group or a phenyl group;

R represents OH, $OR^{10}$ or $OCOR^{11}$, wherein $R^{10}$ and $R^{11}$ are as defined above; and (A) $R^2$ and $R^3$ are each independently selected from:
(i) an aromatic or non-aromatic, carbocyclic or heterocyclic group containing from 5 to 10 ring atoms or two rings with each ring containing 5 or 6 ring atoms, wherein the heterocyclic group comprises a heteroatom selected from N, O, and S, and wherein the carbocyclic or heterocyclic group may be unsubstituted or substituted with one or more substituents selected from: Cl, Br, F, OH, $NO_2$, $CF_3$, $C_{1-4}$ alkyl, $SCH_3$, $NHCOCH_3$, $N(R^6)(R^8)$, $OR^{10}$, and $OCOR^{11}$, wherein $R^6$, $R^8$, $R^{10}$ and $R^{11}$ are as defined above,
(ii) Cl;
(iii) Br;
(iv) F;
(v) OH;
(vi) $NO_2$;
(vii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
(viii) $NHCOCH_3$;
(ix) $N(R^6)(R^8)$, wherein $R^6$ is defined above;
(x) $SR^{10}$, wherein $R^{10}$ is as defined above;
(xi) $OR^{10}$, wherein $R^{10}$ is as defined above; and
(xii) $OCOR^{11}$, wherein $R^{11}$ is as defined above; or (B) $R_2$ and $R_3$ taken together with the carbon atoms to which they are attached form a saturated or unsaturated, carbocyclic or heterocyclic ring having 5 or 6 ring atoms, wherein the heterocyclic group comprises a heteroatom selected from N, O or S, and wherein the carbocyclic or heterocyclic group may be unsubstituted or substituted with one or more substituents selected from Cl, Br, F, OH, $NO_2$, $CF_3$, $C_{1-4}$ alkyl, $SCH_3$, $NHCOCH_8$, $N(R^6)(R^8)$, $OR^{10}$ and $OCOR^{11}$, wherein $R^6$, $R^8$, $R^{10}$ and $R^{11}$ are as defined above.

25. A method of treating neoplasms in a patient comprising administering to said patient a compound of Formula (I):

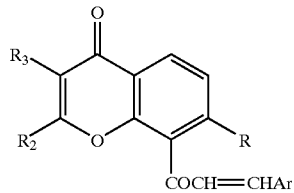

(I)

or a pharmaceutically acceptable salt or solvate thereof wherein:

Ar represents an aromatic or non-aromatic, carbocyclic or heterocyclic group having from 5 to 10 ring atoms or two rings with each ring containing 5 or 6 ring atoms, wherein the heterocyclic group comprises a heteroatom selected from N, O and S, and wherein the carbocyclic or heterocyclic group may be unsubstituted or substituted with one or more substituents selected from: (a) Cl, (b) Br, (c) F, (d) OH, (e) $NO_2$, (f) $CF_3$, (g) $C_{1-4}$ alkyl, (h) $SCH_3$, (i) $NHCOCH_3$, (j) $N(R^6)(R^8)$, wherein $R^6$ and $R^8$ are the same or different and each represents H or $C_{1-4}$ alkyl, (k) $OR^{10}$, wherein $R^{10}$ represents a saturated or unsaturated $C_{1-6}$ straight or branched hydrocarbyl group which may be unsubstituted or substituted with from 1 to 3 substituents selected from: Cl, Br, F, OMe, $NO_2$, and $CF_3$, and (1) —$OCOR^{11}$, wherein $R^{11}$ represents a saturated or unsaturated $C_{1-6}$ straight or branched hydrocarbyl group or a phenyl group;

R represents OH, $OR^{10}$ or $OCOR^{11}$, wherein $R^{10}$ and $R^{11}$ are as defined above; and (A) $R^2$ and $R^3$ are each independently selected from:
(i) an aromatic or non-aromatic, carbocyclic or heterocyclic group containing from 5 to 10 ring atoms or two rings with each ring containing 5 or 6 ring atoms, wherein the heterocyclic group comprises a heteroatom selected from N, O, and S, and wherein the carbocyclic or heterocyclic group may be unsubstituted or substituted with one or more substituents selected from: Cl, Br, F, OH, $NO_2$, $CF_3$, $C_{1-4}$ alkyl, $SCH_3$, $NHCOCH_3$, $N(R^6)(R^8)$, $OR^{10}$, and $OCOR^{11}$, wherein $R^6$, $R^8$, $R^{10}$ and $R^{11}$ are as defined above,
(ii) Cl;
(iii) Br;
(iv) F;
(v) OH;
(vi) $NO_2$;
(vii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
(viii) $NHCOCH_3$;
(ix) $N(R^6)(R^8)$, wherein $R^6$ is defined above;
(x) $SR^{10}$, wherein $R^{10}$ as defined above;
(xi) $OR^{10}$, wherein $R^{10}$ as defined above; and
(xii) $OCOR^{11}$, wherein $R^{11}$ is as defined above; or (B) R₂ and R₃ taken together with the carbon atoms to which they are attached form a saturated or unsaturated, carbocyclic or heterocyclic ring having 5 or 6 ring atoms, wherein the heterocyclic group comprises a heteroatom selected from N, O or S, and wherein the carbocyclic or heterocyclic group may be unsubstituted or substituted with one or more substituents selected from Cl, Br, F, OH, NO₂, CF₃, $C_{1-4}$ alkyl, SCH₃, NHCOCH₈, N(R⁶)(R⁸), OR¹⁰ and OCOR¹¹, wherein R⁶, R⁸, R¹⁰ and R¹¹ are as defined above.

26. The method of claim 25, wherein the neoplasms are located in the uterus, ovary, or breast.

27. The method of claim 24, wherein the cancer is a paclitaxel and docetaxel resistant cancer.

28. The method of claim 25, further comprising administering one or more antineoplastic agents.

29. The method of claim 28, wherein the antineoplastic agent comprises paclitaxel or docetaxel.

30. A method of treating menopausal disorders and osteoporosis in a patient comprising administering to said patient a compound of Formula (I):

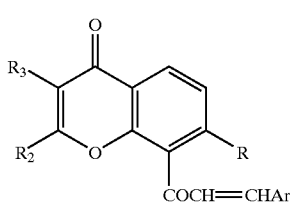

(I)

or a pharmaceutically acceptable salt or solvate thereof wherein:
  Ar represents an aromatic or non-aromatic, carbocyclic or heterocyclic group having from 5 to 10 ring atoms or two rings with each ring containing 5 or 6 ring atoms, wherein the heterocyclic group comprises a heteroatom selected from N, O and S, and wherein the carbocyclic or heterocyclic group may be unsubstituted or substituted with one or more substituents selected from: (a) Cl, (b) Br, (c) F, (d) OH, (e) NO₂, (f) CF₃, (g) $C_{1-4}$ alkyl, (h) SCH₃, (i) NHCOCH₃, (j) N(R⁶)(R⁸), wherein R⁶ and R⁸ are the same or different and each represents H or $C_{1-4}$ alkyl, (k) OR¹⁰, wherein R¹⁰ a saturated or unsaturated $C_{1-6}$ straight or branched hydrocarbyl group which may be unsubstituted or substituted with from 1 to 3 substituents selected from: Cl, Br, F, OMe, NO₂, and CF₃, and (1) —OCOR¹¹, wherein R¹¹ represents a saturated or unsaturated $C_{1-6}$ straight or branched hydrocarbyl group or a phenyl group;
  R represents OH, OCOR¹¹, wherein R¹⁰ and R¹¹ are as defined above; and
  (A) R² and R³ are each independently selected from:
    (i) an aromatic or non-aromatic, carbocyclic or heterocyclic group containing from 5 to 10 ring atoms or two rings with each ring containing 5 or 6 ring atoms, wherein the heterocyclic group comprises a heteroatom selected from N, O and S, and wherein the carbocyclic or heterocyclic group may be unsubstituted or substituted with one or more substituents selected from: Cl, Br, F, OH, NO₂, CF₃, $C_{1-4}$ alkyl, SCH₃, NHCOCH₃, N(R⁶)(R⁸), OR¹⁰, and OCOR¹¹, wherein R⁶, R⁸, R¹⁰ and R¹¹ are as defined above,
    (ii) Cl;
    (iii) Br;
    (iv) F;
    (v) OH;
    (vi) NO₂;
    (vii) a saturated or unsaturated $C_{1-6}$ straight or branched hydrocarbyl group which may be unsubstituted or substituted with from 1 to 3 substituents selected from Cl, Br, F, OMe, NO₂ and CF₃;
    (viii) NHCOCH₃;
    (ix) N(R⁶)(R⁸), wherein R⁶ is defined above;
    (x) SR¹⁰, wherein R¹⁰ as defined above;
    (xi) OR¹⁰, wherein R¹⁰ as defined above; and
    (xii) OCOR¹¹, wherein R¹¹ is as defined above; or
  (B) R₂ and R₃ taken together with the carbon atoms to which they are attached form a saturated or unsaturated, carbocyclic or heterocyclic ring having 5 or 6 ring atoms, wherein the heterocyclic group comprises a heteroatom selected from N, O or S, and wherein the carbocyclic or heterocyclic group may be unsubstituted or substituted with one or more substituents selected from Cl, Br, F, OH, NO₂, CF₃, $C_{1-4}$ alkyl, SCH₃, NHCOCH₈, N(R⁶)(R⁸), OR¹⁰ and OCOR¹¹, wherein R⁶, R⁸, R¹⁰ and R¹¹ are as defined above.

31. A pharmaceutical composition comprising the compound of claim 1 and a pharmaceutically acceptable excipient.

32. A pharmaceutical composition comprising a compound of

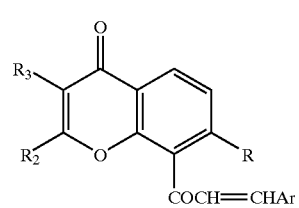

(I)

or a pharmaceutically acceptable salt or solvate thereof wherein:
  Ar represents an aromatic or non-aromatic, carbocyclic or heterocyclic group having from 5 to 10 ring atoms or two rings with each ring containing 5 or 6 ring atoms, wherein the heterocyclic group comprises a heteroatom selected from N, O and S, and wherein the carbocyclic or heterocyclic group may be unsubstituted or substituted with one or more substituents selected from: (a) Cl, (b) Br, (c) F, (d) OH, (e) NO₂, (f) CF₃, (g) $C_{1-4}$ alkyl, (h) SCH₃, (i) NHCOCH₃, (j) N(R⁶)(R⁸), wherein R⁶ and R⁸ are the same or different and each represents H or $C_{1-4}$ alkyl, (k) OR¹⁰, wherein R¹⁰ represents a saturated or unsaturated $C_{1-6}$ straight or branched hydrocarbyl group which may be unsubstituted or substituted with from 1 to 3 substituents selected from: Cl, Br, F, OMe, NO₂, and CF₃, and (1) —OCOR¹¹, wherein R¹¹ represents a saturated or unsaturated $C_{1-6}$ straight or branched hydrocarbyl group or a phenyl group;
  R represents OH, OR¹⁰ or OCOR¹¹, wherein R¹⁰ and R¹¹ are as defined above; and
  (A) R² and R³ are each independently selected from:
    (i) an aromatic or non-aromatic, carbocyclic or heterocyclic group containing from 5 to 10 ring atoms or two rings with each ring containing 5 or 6 ring atoms, wherein the heterocyclic group comprises a heteroatom selected from N, O, and S, and wherein the carbocyclic or heterocyclic group may be unsubstituted or substituted with one or more substituents selected from: Cl, Br, F, OH, $NO_2$, $CF_3$, $C_{1-4}$ alkyl, $SCH_3$, $NHCOCH_3$, $N(R^6)(R^8)$, $OR^{10}$, and $OCOR^{11}$, wherein $R^6$, $R^8$, $R^{10}$ and $R^{11}$ are as defined above, (ii) Cl;
(iii) Br;
(iv) F;
(v) OH;
(vi) $NO_2$;
(vii) a saturated or unsaturated $C_{1-6}$ straight or branched hydrocarbyl group which may be unsubstituted or substituted with from 1 to 3 substituents selected from Cl, Br, F, OMe, $NO_2$ and $CF_3$;
(viii) $NHCOCH_3$;
(ix) $N(R^6)(R^8)$, wherein $R^6$ is defined above;
(x) $SR^{10}$, wherein $R^{10}$ is as defined above;
(xi) $OR^{10}$, wherein $R^{10}$ is as defined above; and
(xii) $OCOR^{11}$, wherein R is as defined above; or (B) $R_2$ and $R_3$ taken together with the carbon atoms to which they are attached form a saturated or unsaturated, carbocyclic or heterocyclic ring having 5 or 6 ring atoms, wherein the heterocyclic group comprises a heteroatom selected from N, O or S, and wherein the carbocyclic or heterocyclic group may be unsubstituted or substituted with one or more substituents selected from Cl, Br, F, OH, $NO_2$, $CF_3$, $C_{1-4}$ alkyl, $SCH_3$, $NHCOCH_8$, $N(R^6)(R^8)$, $OR^{10}$ and $OCOR^{11}$, wherein $R^6$, $R^8$, $R^{10}$ and $R^{11}$ are as defined above; and further comprising one or more antineoplastic agents.

33. The pharmaceutical composition of claim 32, wherein the antineoplastic agent is selected from paclitaxel or docetaxel.

* * * * *

UNITED STATES PATENT AND TRADEMARK OFFICE
CERTIFICATE OF CORRECTION

PATENT NO.    : 6,620,842 B2
DATED         : September 16, 2003
INVENTOR(S)   : Ezio Bombardelli and Piero Valenti It is certified that error appears in the above-identified patent and that said Letters Patent is hereby corrected as shown below:

<u>Title page,</u>
Item [75], Inventors, replace "Milan" with -- Milano --.
Item [73], Assignee, replace "Milan" with -- Milano --.

<u>Column 17,</u>
Line 49, insert the word -- wherein -- between the terms "$OCOR^{11}$," and "$R^{10}$".
Line 51, insert the word -- and -- between the terms "$R^2$" and "$R^3$".

<u>Column 19,</u>
Line 14, replace "heterocylcic" with -- heterocyclic --.

<u>Column 20,</u>
Line 16, replace "-CH=CH" with -- CH≡CH --.
Lines 55-56, replace "1-[3-methyl-7-(2-methylallyloxy)flavon-a-yl]-3-phenylpropen-1-one" with -- 1-[3-methyl-7-(2-methylallyloxy)flavon-8-yl]-3-phenylpropene-1-one --.
Lines 59-60, replace "1-[3-methyl-7-(2-methylallyloxy)flavon-8-yl]-3-(3-methoxy-phenyl)-propen-1-one" with -- 1-[3-methyl-7-(2-methylallyloxy)flavon-8-yl]-3-(3,4,5-tri-methoxy-phenyl)-propen-1-one --.

<u>Column 23,</u>
Line 9, replace "$NHCOCH_8$" with -- $NHCOCH_3$ --.
Line 53, insert the term -- $OR^{10}$, -- between the terms "OH," and "$OCOR^{11}$".

<u>Column 26,</u>
Line 4, replace "R" with -- $R^{11}$ --.

Signed and Sealed this

Fourth Day of November, 2003

JAMES E. ROGAN
*Director of the United States Patent and Trademark Office*